United States Patent
Lanar et al.

(10) Patent No.: US 7,150,875 B2
(45) Date of Patent: Dec. 19, 2006

(54) **RECOMBINANT *PLASMODIUM VIVAX* MEROZOITE PROTEIN-1 P42 VACCINE**

(75) Inventors: David E. Lanar, Takoma Park, MD (US); Sheetij Dutta, Silver Spring, MD (US); Lisa A. Ware, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 128 days.

(21) Appl. No.: 10/100,699

(22) Filed: Mar. 18, 2002

(65) Prior Publication Data

US 2003/0157650 A1 Aug. 21, 2003

Related U.S. Application Data

(60) Provisional application No. 60/277,002, filed on Mar. 19, 2001.

(51) Int. Cl.
*A61K 39/015* (2006.01)
*A61K 39/00* (2006.01)
*A61K 39/002* (2006.01)
*C07H 21/04* (2006.01)
*C12P 21/02* (2006.01)

(52) U.S. Cl. .............. 424/272.1; 424/192.1; 424/191.1; 424/184.1; 536/23.1; 536/23.4; 435/69.5; 435/69.7

(58) Field of Classification Search ............ 424/199.1, 424/268.1, 272.1, 191.1, 185.1, 184.1, 269.1, 424/192.1; 635/69.1, 69.3, 320.3, 172.3; 530/300, 350; 536/23.1, 23.7, 23.4; 435/69.1, 435/69.7, 69.5
See application file for complete search history.

(56) References Cited

FOREIGN PATENT DOCUMENTS

WO WO 9730159 A 8/1997
WO WO 99/56755 * 11/1999

OTHER PUBLICATIONS

Gasser et al 1999. American Journal of Tropical Medicine and Hygiene, (Sep. 1999) vol. 61, No. 3 SUPPL., pp. 492.*
Holm et al, 1 997. Molecular and Biochemical Parasitology, 89, p. 313-319.*
Genton et al 2000, vaccine 18: 2504-2511.*
Chang et al 1996 (Infec.Immun; 64 253-261).*
Cooper, J. A. 1993, Parasitol. Today 9:50-54.*
Chitarra et al 1999 Mol. Cell 3:457-464.*
Ling, et al 1994. Parasite Immunol. 16:63-67.*
Ling et al 1995 Parasite Immunol. 17:425-433.*
Egan et al 1997. Infect. Immun. 65:3024-3031.*
Sachdeva et al Infection and Immunity 2004, 72; 5775-5782.*
Longacre, S. et al., 1994. Plasmodium vivax merozoite surface protein 1 C-terminal recombinant proteins in baculovirus. Molecular and Biochemical Parasitoloty, 64, p. 191-205.
Dutta, S. et al., 2001. Purification, characterization, and immunogenicity of a disulfide cross-linked Plasmodium vivax vaccine candidate antigen, merozoite surface protein 1, expressed in *Eshcerichia coli*. Infection and Immunity 69, p. 5464-5470.

* cited by examiner

*Primary Examiner*—Nita Minnifield
*Assistant Examiner*—Padma Baskar
(74) *Attorney, Agent, or Firm*—Elizabeth Arwine

(57) ABSTRACT

In this application is the expression and purification of a recombinant *Plasmodium vivax* (SalI) PvMSP-1 p42. The method of the present invention produces a highly purified protein which retains folding and disulfide bridging of the native molecule. The recombinant PvMSP-1 p42 is useful as a diagnostic reagent, for use in antibody production, and as a vaccine.

14 Claims, 4 Drawing Sheets

Fluorescence | Phase

Fluorescence | Phase

SEQUENCE LISTING

<160> NUMBER OF SEQ ID NOS: 7

<210> SEQ ID NO 1
<211> LENGTH: 1139
<212> TYPE: DNA
<213> ORGANISM: P. vivax

<400> SEQUENCE: 1

```
gaccaagtaa caacgggaga ggcagaatct gaggcgcctg                   40
agatcctcgt gccagcagga atcagcgatt acgatgtggt                   80
ctacttaaag ccattagccg gaatgtacaa aacgataaag                  120
aagcaattgg aaaatcacgt aaacgcattt aacactaaca                  160
taacggatat gttagactct agactgaaga agagaaacta                  200
cttcttagaa gttctgaact ctgatttgaa cccatttaag                  240
tattcatcat ctggtgagta catcattaag gacccataca                  280
agctgctcga cttggagaag aagaagaagc ttataggcag                  320
ctacaagtac atcggtgcat cgatcgacat ggatctggcc                  360
accgcgaatg atggcgtgac ctactacaac aagatggggg                  400
```

-continued

| | |
|---|---|
| agctctacaa gacgcacttg gatggagtga aaacagagat | 440 |
| taagaaagtc gaagatgata ttaaaaagca agatgaggaa | 480 |
| cttaaaaagt taggaaatgt taacagtcaa gatagtaaaa | 520 |
| agaacgaatt tattgccaaa aaggccgagc tggagaagta | 560 |
| cctcccgttc ctgaatagcc tccaaaagga gtacgagtcc | 600 |
| ctcgtgagca aggtgaacac ctacacagac aacctaaaaa | 640 |
| aagtcatcaa caactgccag ctggagaaaa aggaagccga | 680 |
| gatcactgta aagaaattgc aggactacaa caagatggat | 720 |
| gagaagttgg aggagtacaa aaaatcggag aaaaaaaatg | 760 |
| aagtgaagtc ttctggtctt ctggaaaaat tgatgaaatc | 800 |
| aaaattgatt aaagaaaacg agtccaagga aatattatcc | 840 |
| cagctgctaa atgtgcaaac tcagttatta actatgagct | 880 |
| ccgagcacac atgtatagac accaatgtgc ctgataatgc | 920 |
| agcctgctat aggtacttgg acggaacgga agaatggaga | 960 |
| tgcttgttaa cctttaaaga agaaggcggc aagtgtgtgc | 1000 |
| cagcatcgaa tgtgacttgt aaggataaca atggtggttg | 1040 |
| tgcccctgaa gctgaatgta aaatgacgga cagcaataaa | 1080 |
| tcgtctgtaa atgtactaaa gaaggttctg agccactctt | 1120 |
| tgagggagtt ttctgtagc | 1139 |

<210> SEQ ID NO 2
<211> LENGTH: 379
<212> TYPE: PRT
<213> ORGANISM: P. vivax

<400> SEQUENCE: 2

Asp Gln Val Thr Thr Gly Glu Ala Glu Ser
1               5                   10

Glu Ala Pro Glu Ile Leu Val Pro Ala Gly
            15                  20

Ile Ser Asp Tyr Asp Val Val Tyr Leu Lys
            25                  30

Pro Leu Ala Gly Met Tyr Lys Thr Ile Lys
            35                  40

Lys Gln Leu Glu Asn His Val Asn Ala Phe
            45                  50

Asn Thr Asn Ile Thr Asp Met Leu Asp Ser
            55                  60

Arg Leu Lys Lys Arg Asn Tyr Phe Leu Glu
            65                  70

Val Leu Asn Ser Asp Leu Asn Pro Phe Lys
            75                  80

Tyr Ser Ser Ser Gly Glu Tyr Ile Ile Lys
            85                  90

Asp Pro Tyr Lys Leu Leu Asp Leu Glu Lys
            95                  100

Lys Lys Lys Leu Ile Gly Ser Tyr Lys Tyr
            105                 110

```
Ile Gly Ala Ser Ile Asp Met Asp Leu Ala
            115                 120

Thr Ala Asn Asp Gly Val Thr Tyr Tyr Asn
            125                 130

Lys Met Gly Glu Leu Tyr Lys Thr His Leu
            135                 140

Asp Gly Val Lys Thr Glu Ile Lys Lys Val
            145                 150

Glu Asp Asp Ile Lys Lys Gln Asp Glu Glu
            155                 160

Leu Lys Lys Leu Gly Asn Val Asn Ser Gln
            165                 170

Asp Ser Lys Lys Asn Glu Phe Ile Ala Lys
            175                 180

Lys Ala Glu Leu Glu Lys Tyr Leu Pro Phe
            185                 190

Leu Asn Ser Leu Gln Lys Glu Tyr Glu Ser
            195                 200

Leu Val Ser Lys Val Asn Thr Tyr Thr Asp
            205                 210

Asn Leu Lys Lys Val Ile Asn Asn Cys Gln
            215                 220

Leu Glu Lys Lys Glu Ala Glu Ile Thr Val
            225                 230

Lys Lys Leu Gln Asp Tyr Asn Lys Met Asp
            235                 240

Glu Lys Leu Glu Glu Tyr Lys Lys Ser Glu
            245                 250

Lys Lys Asn Glu Val Lys Ser Ser Gly Leu
            255                 260

Leu Glu Lys Met Lys Ser Lys Leu Ile Lys
            265                 270

Glu Asn Glu Ser Lys Glu Ile Leu Ser Gln
            275                 280

Leu Leu Asn Val Gln Thr Gln Leu Leu Thr
            285                 290

Met Ser Ser Glu His Thr Cys Ile Asp Thr
            295                 300

Asn Val Pro Asp Asn Ala Ala Cys Tyr Arg
            305                 310

Tyr Leu Asp Gly Thr Glu Glu Trp Arg Cys
            315                 320

Leu Leu Thr Phe Lys Glu Glu Gly Gly Lys
            325                 330

Cys Val Pro Ala Ser Asn Val Thr Cys Lys
            335                 340

Asp Asn Asn Gly Gly Cys Ala Pro Glu Ala
            345                 350

Glu Cys Lys Met Thr Asp Ser Asn Lys Ile
            355                 360

Val Cys Lys Cys Thr Lys Glu Gly Ser Glu
            365                 370

Pro Leu Phe Glu Gly Val Phe Cys Ser
```

```
<210> SEQ ID NO 3
<211> LENGTH: 18
<212> TYPE: PRT
<213> ORGANISM: Artificial sequence
<220> FEATURE:
<223> OTHER INFORMATION: vector sequence

<400> SEQUENCE: 3

Met Ala His His His His His His Pro Gly
                5                   10
Gly Ser Gly Ser Gly Thr Met Ala
                15

<210> SEQ ID NO 4
<211> LENGTH: 33
<212> TYPE: DNA
<213> ORGANISM: Artificial sequence
<220> FEATURE:
<223> OTHER INFORMATION: primer sequence

<400> SEQUENCE: 4
cgtgaattca tggaccaagt aacaacggga gag                              33

<210> SEQ ID NO 5
<211> LENGTH: 31
<212> TYPE: DNA
<213> ORGANISM: Artificial sequence
<220> FEATURE:
<223> OTHER INFORMATION: primer sequence

<400> SEQUENCE: 5
acgtctgcag attaaacgtc catgcacagg a                                31

<210> SEQ ID NO 6
<211> LENGTH: 29
<212> TYPE: DNA
<213> ORGANISM: Artificial sequence
<220> FEATURE:
<223> OTHER INFORMATION: primer sequence

<400> SEQUENCE: 6
catgccatgg cagaccaaga acaacggga                                   29

<210> SEQ ID NO 7
<211> LENGTH: 31
<212> TYPE: DNA
<213> ORGANISM: Artificial sequence
<220> FEATURE:
<223> OTHER INFORMATION: primer sequence

<400> SEQUENCE: 7
aatagtttag cggccgctta gctacagaaa c                                31
```

RECOMBINANT PLASMODIUM VIVAX MEROZOITE PROTEIN-1 P42 VACCINE

This application claims the benefit for priority under 35 U.S.C. Section 119(e) from U.S. Provisional Application No. 60/277,002 filed Mar. 19, 2001.

INTRODUCTION

Plasmodium vivax is one of the two major human malaria parasites and alone is responsible for 40–50% of all malaria cases in Latin America and SE Asia. The emergence of drug resistant P. vivax strains (Barat and Bloland, 1997, Infect. Dis. Clin. North Am. 11, 969–987) has underlined the need for a vaccine. Progress towards a vaccine to prevent P. vivax infection is severely constrained by the availability of recombinant P. vivax antigens suitable for efficacy trials in humans. The choice of an expression system for the production of any recombinant protein is critical, particularly if it contains conformational epitopes stabilized by multiple disulphide bonds. Conventionally, Escherichia coli is considered unsuitable for the expression of such structured antigens because of its reducing cytoplasmic environment (Bessette eg al., 1999, Proc. Natl. Acad. Sci. USA 96, 13703–13708). For that reason many P. vivax antigens containing complex tertiary domain structures have been expressed in eukaryotic systems such as yeast (Burghaus and Holder, 1994, Mol. Biochem Parasitol. 64, 165–169; Burns et al., 1997, Infect. Immun. 65, 3138–3145; Chitarra et al, 1999, Mol. Cell 3, 457–464) and baculovirus (Collins et al., 1999, Am. J. Trop. Med. Hyg. 60, 350–356; Cooper, J. A., 1993, Parasitol. Today 9, 50–54). Efforts have been underway to develop an E. coli strain with an oxidative internal environment. One such modified E. coli strain (Origami™), was recently reported to allow disulfide bond formation of recombinant proteins expressed in its cytoplasm (Dieckmann-Schuppert et al., 1992, Eur. J. Biochem. 205, 815–825). Using this strain of E. coli we report production of a soluble 42 kDa fragment of the P. vivax merozoite surface protein-1 (PvMSP-1 p42), a malaria vaccine candidate that requires the formation of multiple disulphide bonds for correct folding.

Merozoite surface protein-1 (MSP-1) is found on the surface of merozoites throughout the genus Plasmodium. In P. falciparum it has been shown that MSP-1 is synthesized as a 195 kDa precursor, it is processed by several proteolytic steps during schizont rupture and merozoite invasion. The 195 kDa protein is cleaved to 83 kDa (p83) and a 42 kDa fragment (p42); the latter is further cleaved to an 11 kDa C-terminal (p19) and a 33 kDa (p33) fragment (reviewed in Dutta, et al., 2000, Mol. Biochem. Parasitol. 109, 179–184). The p19 region contains conserved cysteines that are cross-linked by multiple disulphide linkages forming two epidermal growth factor-like (EGF) domains (Egan et al., 1997, Infect. Immunol. 65, 3024–3031). It has been shown in rodent models of malaria that the presence of the two EGF-like domains in the p19 region is critical for the induction of MSP-1 based protective immunity (Ellman, G. L., 1959, Arch. Biochem. Biophys. 82, 70–77; Gibson et al., 1992, Mol. Biochem. Parasitol. 50, 325–333). In addition, it has been shown that immunization with recombinant P. vivax MSP-1 p19, made in baculovirus infected insect cells, can protect monkeys against parasite challenge (Golding et al., 1994, Am. J. Trop. Med. Hyg. 50 (Suppl.),33–40; Hisaeda et al., 2000, Infect. Immun. 68, 6618–6623). Although the p33 region has not been shown to be critical for protection, several immuno-dominant B and T cell epitopes have been mapped to it, these epitopes are highly immunogenic during natural malaria infection in humans (Kaslow and Kumar, 1996, Immunol. Lett. 51, 187–189). A baculovirus expressed P. cynomolgi MSP-1 p42 construct protected rhesus monkeys against homologous challenge (Kocken et al., 1999, Infect. Immun. 67, 43–49). Given the close evolutionary relationship between the two species we have chosen to express the P. vivax equivalent of this P. cynomolgi p42 construct in E. coli. Initial attempts to express this protein in the conventional E. coli expression host such as BL-21 resulted in the majority of the product being insoluble, however, we found that a 'redox modified' E. coli strain (Origami™) expressed the same protein almost completely in the soluble fraction. We describe here the expression conditions and purification methodology to obtain the PvMSP-1p42 product of high purity and low endotoxin content. In addition, we examine the humoral and cellular immune response of mice to this vaccine candidate protein using two human-use approved adjuvants, Montanide ISA51 and Montanide ISA720.

SUMMARY OF THE INVENTION

The present invention provides isolated and purified P. vivax MSP-1p42 (PvMSP-1 p42) and a method for proper expression and purification of the PvMSP-1 p42. The method of the present invention results in elimination of contaminating proteins and conservation of the native folding and disulfide bridging of the protein. Therefore, the essentially purified PvMSP-1 p42 protein of the present invention retains proper conformation for optimal reactivity for vaccine and screening purposes.

Therefore, a major aim of the present invention resides in the production of large amounts of PvMSP-1 p42 which maintain conformational epitopes critical to epitope formation in pure form (>95% pure) for diagnostic, prophylactic and therapeutic purposes.

This may not seem complicated but, as with most strategies for protein purification, proved to be difficult and unpredictable. E. coli was chosen as a host, even though it had gone out of favor, for two reasons: (1) E. coli was known to produce high level of recombinant proteins and (2) recombinant proteins produced in E. coli are not glycosylated, which is consistent with the capabilities of malaria parasites. Several hurdles had to be overcome to achieve the desired expression level in soluble cytoplasmic form which can be sufficiently purified from host cell proteins without sacrificing proper folding of the protein. Problems with E. coli oxidative cytoplasm and E. coli endotoxin levels, antibiotic resistance and the presence of non-PvMSP-1 p42 contaminants had to be resolved.

Therefore, it is an object of the present invention to provide a recombinant PvMSP-1 p42 for use in diagnostic assays and for production of antibodies.

It is another object of the present invention to provide compositions comprising purified recombinant PvMSP-1 p42.

It is yet another object of the present invention to provide novel vector constructs for recombinantly expressing PvMSP-1 p42, as well as host cells transformed with said vector.

It is also an object of the present invention to provide a method for producing and purifying recombinant PvMSP-1 p42 protein comprising:

growing a host cell containing a vector expressing PvMSP-1 p42 proteins in a suitable culture medium, causing expression of said vector sequence as defined above under suitable conditions for production of soluble protein and, lysing said transformed host cells and recovering said PvMSP-1 p42 protein such that it retains its native folding and is essentially free of host toxins.

It is also an object of the present invention to provide diagnostic and immunogenic uses of the recombinant PvMSP-1 p42 protein of the present invention, as well as to provide kits for diagnostic use for example in malaria screening and confirmatory antibody tests.

It is also an object of the present invention to provide monoclonal or polyclonal antibodies, more particularly human monoclonal antibodies or mouse monoclonal antibodies which are humanized, which react specifically with PvMSP-1 p42 epitopes, either comprised in peptides or conformational epitopes comprised in recombinant proteins.

It is also an object of the present invention to provide possible uses of anti-PvMSP-1 p42 monoclonal antibodies for malaria antigen detection or for therapy of chronic malaria infection.

It is yet another object of the present invention to provide a malaria vaccine comprising PvMSP-1 p42 of the present invention, in an amount effective to elicit an immune response in an animal against *P. vivax;* and a pharmaceutically acceptable diluent, carrier, or excipient.

It is another object of the present invention to provide a malaria DNA vaccine comprising a *Plasmodium vivax* p42 DNA. It is another object of the present invention to provide a method for eliciting in a subject an immune response against malaria, the method comprising administering to a subject a DNA fragment comprising a *P. vivax* MSP-1 p42 DNA.

It is another object of the present invention to provide a method for eliciting in a subject an immune response against malaria, the method comprising administering to a subject a composition comprising PvMSP-1 p42 of the present invention.

It is another object of the present invention to provide a method for preventing malaria infection in an animal comprising administering to the animal the PvMSP-1 p42 of the present invention.

The vaccine according to the present invention is inherently safe, is not painful to administer, and should not result in adverse side effects to the vaccinated individual.

The present invention also provides vectors for the production of a recombinant PvMSP-1 p42, host cells containing the vectors, a method for fermenting and inducing the host cells, and a method for isolating and purifying the recombinant protein. Also provided is a method for bulk fermentation and expression of PvMSP-1 p42.

All the objects of the present invention are considered to have been met by the embodiments as set out below.

DETAILED DESCRIPTION

Figure 1A:
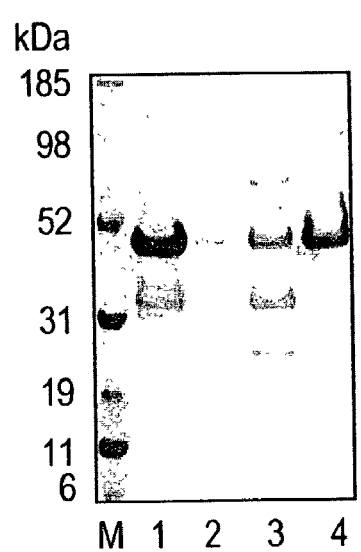
FIGS. 1A, 1B, and 1C. (A)Coomassie blue stained reduced SDS-PAGE of PvMSP-1 p42 partially purified on a 0.5 ml Ni-NTA agarose column under identical conditions from the soluble and insoluble fractions of Origami(DE3) and BL21 strains (1 gm paste each). PvMSP-1 p42 was eluted from each of the 4 columns in equal volume (2 ml) and 20 µl of each was loaded in the wells. Lanes: 1, soluble Origami(DE3); 2, insoluble Origami(DE3); 3, soluble BL21; 4 insoluble BL21 ; M, molecular weight marker. (B)Coomassie blue stained reduced SDS-PAGE (20 µg protein per well). Lanes: 1, Ni-NTA elution; 2, Q-sepharose elution. (C) Anti-*E. coli* immunoblot of the gel shown in FIG. 1B. (2 µg protein per well).

In the description that follows, a number of terms used in recombinant DNA, parasitology and immunology are extensively utilized. In order to provide a clearer and consistent understanding of the specification and claims, including the scope to be given such terms, the following definitions are provided.

In general, an 'epitope' is defined as a linear array of 3–10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type(group)-specific variants, e.g. of the currently known sequences or strains belonging to *Plasmodium* such as Sal I, Belem, Chesson, Vietnam, North Korean, or any other known or newly defined *Plasmodium vivax* strains or field isolates.

The term 'solid phase' intends a solid body to which the individual *P. vivax* antigen is bound covalently or by non-covalent means such as hydrophobic, ionic, or van der Waals association.

The term 'biological sample' intends a fluid or tissue of a mammalian individual (e.g. an anthropoid, a human), reptilian, avian, or any other zoo or farm animal that commonly contains antibodies produced by the individual, more particularly antibodies against malaria. The fluid or tissue may also contain *P. vivax* antigen. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism. Some biological fluids are used as a source of other products, such as clotting factors (e.g. Factor VIII), serum albumin, growth hormone and the like.

The term 'immunologically reactive' means that the antigen in question will react specifically with anti-MSP-1 antibodies present in a body component from a malaria infected individual.

The term 'immune complex' intends the combination formed when an antibody binds to an epitope on an antigen.

The term 'PvMSP-1 p42' as used herein refers to the polymorphic C-terminal 42 kDa protein fragment or polypeptide resulting from the processing by proteases of the 195 kDa membrane-anchored MSP-1 precursor. During merozoite invasion, the 42 kDa fragment is subjected to secondary processing producing a 33-kDa fragment (MSP-1 p33) and a 19 kDa C-terminal fragment, (MSP-1 p19) which remains attached via GPI to the surface of the invading merozoite. The MSP-1 p42 protein extends from approximately amino acid (aa) 1350 to about aa 1729 of the full-length precursor protein (Genbank accession # M75674.1).

The term 'PvMSP-1 p42' as used herein also includes analogs and truncated forms that are immunologically cross-reactive with natural PvMSP-1 p42. By 'PvMSP-1 p42' is intented PvMSP-1 p42 from other strains of *Plasmodium vivax,* or any other newly identified strain or field isolate of *Plasmodium vivax.*

The term 'homo-oligomer' as used herein refers to a complex of PvMSP-1 p42 containing more than one PvMSP-1 p42 monomer, e.g. PvMSP-1 p42/PvMSP-1 p42 dimers, trimers or tetramers, or any higher-order homo-oligomers of PvMSP-1 p42 are all 'homo-oligomers' within the scope of this definition. The oligomers may contain one, two, or several different monomers of PvMSP-1 p42 obtained from different strains of *Plasmodium vivax* including for example Sal I, Belem, Chesson, Vietnam, North Korean, and other strains and field isolates. Such mixed oligomers are still homo-oligomers within the scope of this invention, and may allow more universal diagnosis, prophylaxis or treatment of malaria.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' PvMSP-1 p42 protein intends a *Plasmodium* protein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other *Plasmodium* components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris), Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces.* Also these hosts are contemplated within the present invention.

The term 'higher eukaryote' refers to host cells derived from higher animals, such as mammals, reptiles, insects, and the like. Presently preferred higher eukaryote host cells are derived from Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation : (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against malaria, whether partial or complete. A vaccine may also be useful for treatment of an infected individual, in which case it is called a therapeutic vaccine.

The term 'therapeutic' refers to a composition capable of treating malaria infection. The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation. Preferred ranges of PvMSP-1 p42 for prophylaxis of malaria disease are about 0.01 to 1000 ug/dose, more preferably about 0.1 to 100 ug/dose, most preferably about 10–50 ug/dose. Several doses may be needed per individual in order to achieve a sufficient immune response and subsequent protection against malaria.

More particularly, the present invention contemplates essentially purified PvMSP-1 p42 and a method for isolating or purifying recombinant PvMSP-1 p42 protein, characterized in that upon lysing the transformed host cells to isolate the recombinantly expressed protein, the disulfide bonds necessary for proper folding of the protein are preserved.

The term 'PvMSP-1 p42' refers to a polypeptide or an analogue thereof (e.g. mimotopes) comprising an amino acid sequence (and/or amino acid analogues) defining at least one PvMSP-1 p42 epitope. Typically, the sequences defining the epitope correspond to the amino acid sequence of PvMSP-1 p42 region of *P. vivax* (either identically or via substitution of analogues of the native amino acid residue that do not destroy the epitope). The PvMSP-1 p42 protein corresponds to a nucleotide sequence identified in SEQ ID NO: 1 and spans from amino acid 1350 to 1729 of MSP-1 Sal I allele (SEQ ID NO:2). Upon expression in the parasite system (non-glycosylated), it is believed to have an approximate molecular weight of 42 kDa as determined by SDS-PAGE.

The PvMSP-1 p42 antigen used in the present invention is preferably a full-length protein, or a substantially full-length version, i.e. containing functional fragments thereof (e.g. fragments which are not missing sequence essential to the formation or retention of an epitope). Furthermore, the *P. vivax* antigen of the present invention can also include other sequences that do not block or prevent the formation of the conformational epitope of interest. The presence or absence of a conformational epitope can be readily determined though screening the antigen of interest with an antibody as described in the Examples below (polyclonal serum or monoclonal to the conformational epitope) and comparing its reactivity to that of a denatured version of the antigen which retains only linear epitopes (if any).

The *P. vivax* antigen of the present invention can be made by any recombinant method that provides the epitope of interest. For example, recombinant expression in *E. coli* is a preferred method to provide non-glycosylated antigens in 'native' conformation. This is most desirable because natural *P. vivax* antigens are not glycosylated. Proteins secreted from mammalian cells may contain modifications including galactose or sialic acids which may be undesirable for certain diagnostic or vaccine applications. However, it may also be possible and sufficient for certain applications, as it is known for proteins, to express the antigen in other recombinant hosts such as baculovirus and yeast or higher eukaryotes, as long as glycosylation is inhibited.

The proteins according to the present invention may be secreted or expressed within compartments of the cell. Preferably, however, the proteins of the present invention are expressed within the cell and are released upon lysing the cells.

It is also understood that the isolates used in the examples section of the present invention were not intended to limit the scope of the invention and that an equivalent sequence from a *P. vivax* isolate other than Sal I, i.e. from another strain, e.g. Chesson, Belem, Vietnam, North Korean, and other strains and field isolates, can be used to produce a recombinant PvMSP-1 p42 protein using the methods described in the present application. Other new strains of *Plasmodium* may be a suitable source of PvMSP-1 p42 sequence for the practice of the present invention.

The PvMSP-1 p42 protein of the present invention is expressed as part of a recombinant vector. The present invention relates more particularly to the PvMSP-1 p42 nucleic acid sequence in recombinant nucleic acid pPvMSP1-42, comprising the p42 protein sequence extending from Asp at 1350 to Ser at 1729 of the native PvMSP1 protein linked to 18 vector encoded residues (SEQ ID NO:3) at the N-terminus. The PvMSP-1 p42 genomic sequence was cloned into pETAT(NK2) (kindly provided by Evelina Angov, Walter Reed Army Institute of Research, Silver Spring, Md.). This plasmid comprises, in sequence, a T7 promoter, optionally a lac operator, a ribosome binding site, restriction sites to allow insertion of the structural gene and a T7 terminator sequence. Examples of other plasmids which contain the T7 inducible promoter include the expression plasmids pET-17b, pET-11a, pET-24a–d(+), and pEt-9a, all from Novagen (Madison, Wis.); see the Novagen catalogue.

The present invention also contemplates host cells transformed with a recombinant vector as defined above. In a preferred embodiment, *E. coli* strain Origami(DE3) is employed. The above plasmids may be transformed into this strain or other strains of *E. coli* having the following characteristics: a T7 RNA polymerase rec gene, Lon, ompT protease mutants or any other *E. coli* with a protease deficiency. Preferably, the host includes Origami(DE3) and any of its predecessors that also have a more oxidative internal cell environment. Other host cells such as insect cells can be used taking into account that other cells may result in lower levels of expression.

Eukaryotic hosts include lower and higher eukaryotic hosts as described in the definitions section. Lower eukaryotic hosts include yeast cells well known in the art. Higher eukaryotic hosts mainly include mammalian cell lines known in the art and include many immortalized cell lines available from the ATCC, inluding HeLa cells, Chinese hamster ovary (CHO) cells, Baby hamster kidney (BHK) cells, PK15, RK13 and a number of other cell lines. PvMSP-1 p42 expressed in these cells will be glycosylated unless the cells have been altered such that glycosylation of the recombinant protein is not possible. It is expected that when producing PvMSP-1 p42 in a eukaryotic expression system, extensive investigation into methods for expressing, isolating, purifying, and characterizing the protein would be required as eukaryotic cells post-translationally modify this protein and this would alter protein structure and immunogenicity.

Methods for introducing vectors into cells are known in the art. Please see e.g., Maniatis, Fitsch and Sambrook, *Molecular Cloning; A Laboratory Manual* (1982) or *DNA Cloning,* Volumes I and II (D. N. Glover ed. 1985) for general cloning methods. Host cells provided by this invention include *E. coli* containing pPvMSP1-42.

A preferred method for isolating or purifying PvMSP-1 p42 as defined above is further characterized as comprising at least the following steps:

(i) growing a host cell as defined above transformed with a recombinant vector expressing PvMSP-1 p42 proteins in a suitable culture medium, (ii) causing expression of said vector sequence as defined above under suitable conditions for production of a soluble protein, (iii) lysing said transformed host cells and recovering said PvMSP-1 p42 protein such that it retains its native conformation and is essentially pure.

Once the host has been transformed with the vector, the transformed cells are grown in culture in the presence of the desired antibiotic. For FDA regualtory purposes, it is preferable to use tetracycline or kanamycin. When cells reach optimal biomass density, in this case about 4–6, preferably about 7.0 OD 600, the cells are induced to produce the recombinant protein. The inventors have found after trial and error that for expression of a soluble PvMSP-1 p42, it was necessary to cool the culture to a range of about 10° C.–20° C., more preferably about 15° C.–28° C., most preferably about 24 to 26° C. prior to induction. The concentration of inducer, i.e. IPTG, added affects the maximal protein synthesis. It was found that a concentration of 0.1 mM IPTG was best, however, a range of 0.05 to 0.5 mM would be sufficient to produce 80–100% of maximal.

The cells were then collected and lysed to release the recombinant protein. Preferably, lysis should occur at a paste to buffer ratio of 1:8 w/v to reduce viscosity and volume of sample loaded on Ni-NTA column. Preferably, lysis is in the presence of imidazole, about 40 mM, which reduces non specific binding of *E. coli* protein to Ni resin. Lysis is preferably at a temperature of about 0° C.–24° C., more preferably about 20° C. in order to retain native folding of the PvMSP-1 p42 protein and to reduce proteolysis. A high salt concentration of about 0.5–1.0 M is preferable. Salts used include NaCl, NaP, or other monovalent ions in a pH range from about 6.7 to about 8.3, preferably, between about 7.0 to about 8.0.

Preferably, the *E. coli* endotoxin is separated and removed from the recombinant protein. This can be done several ways. For PvMSP-1 p42, endotoxin was removed by applying to a $Ni^{+2}$-NTA column. The removal of endotoxin depended on washing at low pH, about 5.8 to 6.5, preferably about pH 6.2, in high salt, about 0.5 to about 1.0 mM, preferably about 500 mM NaCl at a flow rate of about 2.0–3.0 ml/min, preferably about 2.5 ml/min. The resin to cell paste ratio can be about 7 ml of matrix to 40 g of paste. The recombinant protein can be eluted by addition of high pH buffer of about 7.5 to about 8.5, preferably about pH 8.0, in a phosphate buffer of about 10–30 mM, more preferably about 20 mM sodium phosphate buffer, in high imidazole, about 400–600 mM, more preferably about 500 mM.

The sample is further purified by ion exchange chromatography, preferably a Q-Sepharose FASTflow column (Amersham Pharmacia Biotech, Piscataway, N.J.) at about 4–6 ml of matrix to about 30–50 g of paste, more preferably, about 5 ml of matrix to about 40 g of paste. The sample is applied to the column and washed in a buffer of about pH 8.0 with about 100 mM NaCl in 20 mM NaP buffer. The PvMSP-1 p42 is eluted with about 200 mM NaCl (about pH 8.0) in 20 mM NaP buffer.

The present invention further relates to a composition comprising PvMSP-1 p42 for use as a vaccine and for in vitro detection of malaria antibodies present in a biological sample.

For in vitro diagnosis of malaria antibodies present in a biological sample, the assay may comprise at least (i) contacting said biological sample with a composition comprising any of the PvMSP-1 p42 proteins or peptides derived from said protein which are immunologically identiable with PvMSP-1 p42, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, and (iv) detecting the presence of said immune complexes visually or mechanically (e.g. by means of densitometry, fluorimetry, colorimetry).

The present invention also relates to a kit for determining the presence of malaria antibodies, in a biological sample, comprising:

at least one peptide or protein composition as defined above, possibly in combination with other polypeptides or peptides from *Plasmodium* or other types of malaria parasite, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against malaria present in the biological sample, means for detecting the immune complexes formed in the preceding binding reaction, and possibly also including an automated scanning and interpretation device for inferring the malaria parasite present in the sample from the observed binding pattern.

The immunoassay methods according to the present invention utilize PvMSP-1 p42 domains that maintain linear (in case of peptides) and conformational epitopes (proteins) recognized by antibodies in the sera from individuals infected with a malaria parasite. PvMSP-1 p42 antigens of the present invention may be employed in virtually any assay format that employs a known antigen to detect antibodies. A common feature of all of these assays is that the antigen is contacted with the body component suspected of containing malaria antibodies under conditions that permit the antigen to bind to any such antibody present in the component. Such conditions will typically be physiologic temperature, pH and ionic strenght using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon.TM.), diazotized paper, nylon membranes, activated beads, and Protein A beads. For example, Dynatech Immunolon.TM.1 or Immunlon.TM. 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are know in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of malaria antibodies in the antibody-antigen complexes is directly monitored. This may be accomplished by determining whether labeled anti-xenogeneic (e.g. anti-human) antibodies which recognize an epitope on anti-malaria antibodies will bind due to complex formation. In a competitive format, the amount of malaria antibodies in the sample is deduced by monitoring the competitive effect on the binding of a known amount of labeled antibody (or other competing ligand) in the complex.

Complexes formed comprising anti-malaria antibody (or in the case of competitive assays, the amount of competing antibody) are detected by any of a number of known techniques, depending on the format. For example, unlabeled malaria antibodies in the complex may be detected using a conjugate of anti-xenogeneic Ig complexed with a label (e.g. an enzyme label).

In an immunoprecipitation or agglutination assay format the reaction between the malaria antigens and the antibody forms a network that precipitates from the solution or suspension and forms a visible layer or film of precipitate. If no anti-malaria antibody is present in the test specimen, no visible precipitate is formed.

There currently exist three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The PvMSP-1 p42 proteins, peptides, or antigens of the present invention will typically be packaged in the form of a kit for use in these immunoassays. The kit will normally contain in separate containers the PvMSP-1 p42 antigen, control antibody formulations (positive and/or negative), labeled antibody when the assay format requires the same and signal generating reagents (e.g. enzyme substrate) if the label does not generate a signal directly. The PvMSP-1 p42 antigen may be already bound to a solid matrix or separate with reagents for binding it to the matrix. Instructions (e.g. written, tape, CD-ROM, etc.) for carrying out the assay usually will be included in the kit.

Immunoassays that utilize the PvMSP-1 p42 antigen are useful in screening blood for the preparation of a supply from which potentially infective malaria parasite is lacking. The method for the preparation of the blood supply comprises the following steps. Reacting a body component, preferably blood or a blood component, from the individual donating blood with PvMSP-1 p42 proteins of the present invention to allow an immunological reaction between malaria antibodies, if any, and the PvMSP-1 p42 antigen. Detecting whether anti-malaria antibody—PvMSP-1 p42 antigen complexes are formed as a result of the reacting. Blood contributed to the blood supply is from donors that do not exhibit antibodies to the native MSP-1 antigens.

The present invention further contemplates the use of PvMSP-1 p42 proteins, or parts thereof as defined above, for in vitro monitoring malaria infection or prognosing the response to treatment (for instance with chloroquine, mefloquine, Malarome) of patients suffering from malaria infection comprising:

incubating a biological sample from a patient with malaria infection with an PvMSP-1 p42 protein or a suitable part thereof under conditions allowing the formation of an immunological complex, removing unbound components, calculating the anti-PvMSP-1 p42 titers present in said sample (for example at the start of and/or during the course of therapy), and monitoring the natural course of malaria infection, or prognosing the response to treatment of said patient on the basis of the amount anti-PvMSP-1 p42 titers found in said sample at the start of treatment and/or during the course of treatment.

Patients who show a decrease of 2, 3, 4, 5, 7, 10, 15, or preferably more than 20 times of the initial anti-PvMSP-1 p42 titers could be concluded to be long-term, sustained responders to malaria therapy.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring malaria infection or prognosing the response to treatment (for instance to medication) of patients suffering from malaria infection comprising:

at least one PvMSP-1 p42 peptide as defined above, a buffer or components necessary for producing the buffer enabling the binding reaction between these proteins or peptides and the anti-PvMSP-1 p42 antibodies present in a biological sample, means for detecting the immune complexes formed in the preceding binding reaction, and possibly also an automated scanning and interpretation device for inferring a decrease of anti-PvMSP-1 p42 titers during the progression of treatment.

The present invention also relates to a serotyping assay for detecting one or more serological types or alleles of malaria parasite present in a biological sample, more particularly for detecting antibodies of the different types or alleles of malaria parasites to be detected combined in one assay format, comprising at least the following steps:

(i) contacting the biological sample to be analyzed for the presence of malaria antibodies of one or more serological types, with at least one of the PvMSP-1 p42 compositions as defined above, preferentially in an immobilized form under appropriate conditions which allow the formation of an immune complex, (ii) removing unbound components, (iii) incubating the immune complexes formed with heterologous antibodies, with said heterologous antibodies being conjugated to a detectable label under appropriate conditions, (iv) detecting the presence of said immune complexes visually or mechanically (e.g. by means of densitometry, fluorimetry, calorimetry) and inferring the presence of one or more malaria serological types present from the observed binding pattern.

It is to be understood that the compositions of proteins or peptides used in this method are recombinantly expressed type-specific or allele-specific proteins or type-specific peptides.

The present invention further relates to a kit for serotyping one or more serological types or alleles of malaria parasite present in a biological sample, more particularly for detecting the antibodies to these serological types of malaria parasites comprising:

at least one PvMSP-1 p42 protein or PvMSP-1 p42 peptide, as defined above, a buffer or components necessary for producing the buffer enabling the binding reaction between these proteins or peptides and the anti-MSP-1 antibodies present in a biological sample, means for detecting the immune complexes formed in the preceding binding reaction, possibly also an automated scanning and interpretation device for detecting the presence of one or more serological types present from the observed binding pattern.

The present invention also relates to the use of a peptide or protein composition as defined above, for immobilization on a solid support and incorporation into a reversed phase hybridization assay, preferably for immobilization as parallel lines onto a solid support such as a membrane strip, for determining the presence or the genotype of malaria parasite according to a method as defined above. Combination with other type-specific or allele-specific antigens from other malaria parasites also lies within the scope of the present invention.

The present invention also relates to an PvMSP-1 p42 specific antibody raised upon immunizing an animal with a peptide or protein composition, with said antibody being specifically reactive with any of the polypeptides or peptides as defined above, and with said antibody being preferably a monoclonal antibody.

The present invention also relates to an PvMSP-1 p42 specific antibody screened from a variable chain library in plasmids or phages or from a population of human B-cells by means of a process known in the art, with said antibody being reactive with any of the polypeptides or peptides as defined above, and with said antibody being preferably a monoclonal antibody.

The PvMSP-1 p42 specific monoclonal antibodies of the invention can be produced by any hybridoma liable to be formed according to classical methods from splenic or lymph node cells of an animal, particularly from a mouse or rat, immunized against the *Plasmodium* polypeptides or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombinant DNA technology, departing from parts of mouse and/or human genomic DNA sequences coding for H and L chains from cDNA or genomic clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with malaria, or vaccinated against malaria. Such human monoclonal antibodies are prepared, for instance, by means of human peripheral blood lymphocytes (PBL) repopulation of severe combined immune deficiency (SCID) mice, or by means of transgenic mice in which human immunoglobulin genes have been used to replace the mouse genes.

The invention also relates to the use of the proteins or peptides of the invention, for the selection of recombinant antibodies by the process of repertoire cloning.

Antibodies directed to peptides or single or specific proteins derived from a certain strain may be used as a medicament, more particularly for incorporation into an immunoassay for the detection of *Plasmodium* strains for detecting the presence of PvMSP-1 p42 antigens, or antigens containing PvMSP-1 p42 epitopes, for prognosing/monitoring of malaria disease, or as therapeutic agents.

Alternatively, the present invention also relates to the use of any of the above-specified PvMSP-1 p42 monoclonal antibodies for the preparation of an immunoassay kit for detecting the presence of PvMSP-1 p42 antigen or antigens containing PvMSP-1 p42 epitopes in a biological sample, for the preparation of a kit for prognosing/monitoring of malaria disease or for the preparation of a malaria medicament.

The present invention also relates to a method for in vitro diagnosis or detection of malaria antigen present in a biological sample, comprising at least (i) contacting said biological sample with any of the PvMSP-1 p42 specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, and (iv) detecting the presence of said immune complexes visually or mechanically (e.g. by means of densitometry, fluorimetry, colorimetry).

The present invention also relates to a kit for in vitro diagnosis of a malaria antigen present in a biological sample, comprising:

at least one monoclonal antibody as defined above, with said antibody being preferentially immobilized on a solid substrate, a buffer or components necessary for producing the buffer enabling binding reaction between these antibodies and the malaria antigens present in the biological sample, and a means for detecting the immune complexes formed in the preceding binding reaction.

The kit can possibly also include an automated scanning and interpretation device for inferring the malaria antigens present in the sample from the observed binding pattern.

Monoclonal antibodies according to the present invention are suitable both as therapeutic and prophylactic agents for treating or preventing malaria infection in susceptible malaria-infected subjects. Subjects include rodents such as mice or guinea pigs, monkeys, and other mammals, including humans.

In general, this will comprise administering a therapeutically or prophylactically effective amount of one or more monoclonal antibodies of the present invention to a susceptible subject or one exhibiting malaria infection. Any active form of the antibody can be administered, including Fab and F(ab')$_2$ fragments. Antibodies of the present invention can be produced in any system, including insect cells, baculovirus expression systems, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before parasite can be controlled, and the induced immune response to the MAbs in the subject does not induce "serum sickness" in the subject. Preferably, the MAbs administered exhibit some secondary functions such as binding to Fc receptors of the subject.

Treatment of individuals having malaria infection may comprise the administration of a therapeutically effective amount of PvMSP-1 p42 antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to PvMSP-1 p42, or an antibody capable of protecting against malaria in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg–100 pg/kg, 100 pg/kg–500 pg/kg, 500 pg/kg–1 ng/kg, 1 ng/kg–100 ng/kg, 100 ng/kg–500 ng/kg, 500 ng/kg–1 ug/kg, 1 ug/kg–100 ug/kg, 100 ug/kg–500 ug/kg, 500 ug/kg–1 mg/kg, 1 mg/kg–50 mg/kg, 50 mg/kg–100 mg/kg, 100 mg/kg–500 mg/kg, 500 mg/kg–1 g/kg, 1 g/kg–5 g/kg, 5 g/kg–10 g/kg (body weight of recipient), although a lower or higher dosage may be administered.

In a similar approach, another prophylactic use of the monoclonal antibodies of the present invention is the active immunization of a patient using an anti-idiotypic antibody raised against one of the present monoclonal antibodies. Immunization with an anti-idiotype which mimics the structure of the epitope could elicit an active anti-PvMSP-1 p42 response (Linthicum, D. S. and Farid, N. R., Anti-Idiotypes, Receptors, and Molecular Mimicry (1988), pp 1–5 and 285–300).

Likewise, active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., $NH_2$-acetylation or COOH-terminal amidation, to provide additional means for coupling or fusing the peptide to another protein or peptide molecule or to a support.

The antibodies capable of protecting against malaria are intended to be provided to recipient subjects in an amount sufficient to effect a reduction in the malaria infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

In another aspect of the invention is provided a DNA vaccine against malaria comprising a nucleic acid encoding PvMSP-1 p42. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

Therefore, the present invention relates to a DNA or cDNA segment which encodes *Plasmodium vivax* p42 as described above. Genome sequences from different strains of *Plasmodium vivax* have been published and are publicly available. Other strains of *P. vivax* are expected to contain sequences at least 90% identical which will likely produce antigens capable of eliciting protective/neutralizing antibodies. Such strains include Belem, Chesson, Vietnam, North Korean, and others. It is envisioned that the PvMSP-1 p42 from strain Sal I will provide cross protection against other *P. vivax* strains due to the high homology between strains in this region.

DNA or nucleic acid sequences to which the invention also relates include fragments of the p42 genes containing protective epitopes or antigenic determinants. Such epitopes may be linear or conformational as shown below in the Examples. The sequence of nucleic acids encoding antigens may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. It is understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the p42 genes of *P. vivax* are equivalents within the scope of the present invention.

The DNA encoding the desired antigen can be introduced into the cell in any suitable form including, the fragment alone, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual* or *DNA Cloning,* Vol. I and II (D. N. Glover, ed., 1985) for general cloning methods.

The DNA, alone or in a vector, can be delivered by injection into the tissue of the recipient, oral or pulmonary delivery and inoculation by particle bombardment (i.e., gene gun) after coating a carrier particle with the DNA vaccine. Any of these methods can be used to deliver DNA as long as the DNA is expressed and the desired antigen is made in the cell.

Generally, the DNA vaccine administered may be in an amount of about 1–5 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The present invention more particularly relates to a composition comprising at least one of the above-specified peptides or a recombinant PvMSP-1 p42 protein composition as defined above, for use as a vaccine for immunizing a mammal, preferably humans, against malaria, comprising administering a sufficient amount of the composition possibly accompanied by pharmaceutically acceptable adjuvant(s), to produce an immune response. The vaccine composition of the present invention is expected to provide cross-protection against infection from other *P. vivax* malaria strains, since the immunogenic antigen p42 is highly conserved between strains.

Immunogenic compositions can be prepared according to methods known in the art. The present compositions comprise an immunogenic amount of a recombinant PvMSP-1 p42 proteins or peptides as defined above, usually combined with a pharmaceutically acceptable carrier, preferably further comprising an adjuvant.

The proteins of the present invention, preferably purified PvMSP-1 p42 derived from pPvMSP1-42, are expected to provide a particularly useful vaccine antigen, since the antigen is able to induce invasion inhibitory antibodies as well as high titer antibodies that react with schizont-infected erythrocytes.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Preferred adjuvants to enhance effectiveness of the composition include, but are not limited to: montanide, aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine(nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the 3 components MPL, TDM or CWS may also be used alone or combined 2 by 2. Additionally, adjuvants such as Stimulon (Cambridge Bioscience, Worcester, Mass.) or SAF-1 (Syntex) may be used. Further, Complete Freund's Adjuvant (CFA) and Incomplete Freund's Adjuvant (IFA) may be used for non-human applications and research purposes.

The immunogenic compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect. The PvMSP-1 p42 proteins of the invention may also be incorporated into Immune Stimulating Complexes together with saponins, for example QuilA (ISCOMS).

Immunogenic compositions used as vaccines comprise a 'sufficient amount' or 'an immunologically effective amount' of the proteins of the present invention, as well as any other of the above mentioned components, as needed. 'Immunologically effective amount', means that the administration of that amount to an individual, either in a single dose or as part of a series, is effective for treatment, as defined above. This amount varies depending upon the health and physical condition of the individual to be treated, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, the strain of malaria infection, and other relevant factors. It is expected that the amount will fall in a relatively broad range that can be determined through routine trials. Usually, the amount will vary from 0.01 to 1000 ug/dose, more particularly from about 1.0 to 100 ug/dose most preferably from about 10 to 50 ug/dose.

The proteins may also serve as vaccine carriers to present homologous (e.g. other malaria antigens, such as EBA-175, PvCSP Type 210, PvCSP Type 247, PvTRAP, PvMSP2, PvMSP4, PvMSP5, PvMSP6, PvMSP7, PvMSP8, PvMSP9, and PvAMA1.) or heterologous (non-malaria) antigens in a multivalent vaccine. In this use, the proteins of the invention provide an immunogenic carrier capable of stimulating an immune response to other antigens. The antigen may be conjugated either by conventional chemical methods, or may be cloned into the gene encoding PvMSP-1 p42 fused to the 5' end or the 3' end of the PvMSP-1 p42 gene. The vaccine may be administered in conjunction with other immunoregulatory agents.

The compounds of the present invention can be formulated according to known methods to prepare pharmaceutically useful compositions, whereby these materials, or their functional derivatives, are combined in admixture with a phamaceutically acceptable carrier vehicle. Suitable vehicles and their formulation, inclusive of other human proteins, e.g., human serum albumin, are described, for example, in *Remington's Pharmaceutical Sciences* (16th ed., Osol, A. ed., Mack Easton Pa. (1980)). In order to form a pharmaceutically acceptable composition suitable for effective administration, such compositions will contain an effective amount of the above-described compounds together with a suitable amount of carrier vehicle.

Additional pharmaceutical methods may be employed to control the duration of action. Control release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions. Such techniques are disclosed in *Remington's Pharmaceutical Sciences* (1980).

Administration of the compounds, whether antibodies or vaccines, disclosed herein may be carried out by any suitable means, including parenteral injection (such as intraperitoneal, subcutaneous, or intramuscular injection), in ovo injection of birds, orally, or by topical application of the antibodies (typically carried in a pharmaceutical formulation) to an airway surface. Topical application of the antibodies to an airway surface can be carried out by intranasal administration (e.g., by use of dropper, swab, or inhaler which deposits a pharmaceutical formulation intranasally). Topical application of the antibodies to an airway surface can also be carried out by inhalation administration, such as by creating respirable particles of a pharmaceutical formulation (including both solid particles and liquid particles) containing the antibodies as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

The treatment may be given in a single dose schedule, or preferably a multiple dose schedule in which a primary course of treatment may be with 1–10 separate doses, followed by other doses given at subsequent time intervals required to maintain and or reinforce the response, for example, at 1–4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

The present invention also provides kits which are useful for carrying out the present invention. The present kits comprise a first container means containing the above-described antibodies. The kit also comprises other container means containing solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The container means may be in another container means, e.g. a box or a bag, along with the written information.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Cloning the PvMSP-1 p42 gene. Genomic DNA of *P. vivax* Sal I strain (kindly provided by Dr. William E. Collins, Centers of Disease Control, Atlanta Ga.) was prepared using the Qiaamp blood kit (Qiagen, Valencia Calif.). Genomic DNA was used as a template for the amplification of PvMSP-1 p42 gene using a set of PCR primers (forward: 5'CGTGAATTCATGGACCAAGTAACAA-CGG-GAGAG3' (SEQ ID NO.:4), reverse: 5'ACGTCTGCAGAT-TAAA-CGTCCATGCACAGGA3' (SEQ ID NO:5)), the PCR product was cloned into a sequencing plasmid and was sequenced. This was then used as a template for amplification of the expression construct using a set of primers (forward: 5'CATGCCATGGCAGACCAAGAA-CAACGGGA3' (SEQ ID NO:6), reverse: 5'AATAGTT-TAGCGGCCGCTTAGCTACAGAAAAC3' (SEQ ID NO:7)). PCR product was ligated to the Nco I-Not I sites of the vector pETAT(NK2) (kindly provided by Dr. Evelina Angov, WRAIR, Silver Spring Md.). The ligation mix was transformed into DH5α cells and recombinant clones were selected on ampicillin. The cloned insert was sequenced and transformed into BL21(DE3) and Origami™(DE3) *E. coli* expression hosts (Novagen, Madison Wis.). The tranformants were selected on ampicillin plates and expression was checked in IPTG induced cultures. Glycerol stocks were made and stored at −70° C. The deduced amino acid sequence of the protein obtained from this plasmid is 18 vector encoded residues on the N-terminus (MAHHHHH-HPGGSGSGTMA (SEQ ID NO:3)) linked to amino acids #$1350_{Asp}$ to $1729_{Ser}$ of the native PvMSP1 protein.

Expression of PvMSP-1 p42 protein. Expression using both the host strains was carried out in a 10 L bioreactor (New Brunswick Scientific NJ). Terrific Broth containing 100 mg ml$^{-1}$ ampicillin or 12.5 μg ml$^{-1}$ tetracycline was inoculated with 100 ml overnight grown seed culture; temperature was maintained at 37° C.; pH 7.2 and agitation at 800 rpm. The cell density ($OD_{600}$) was monitored and temperature was rapidly (<20 min) reduced to 25° C. at an $OD_{600}$ of 7; IPTG was added to a final concentration of 0.1 mM. Induction was carried at 25° C. for 2 hours and cells harvested by centrifugation. Cell paste was weighed and routinely stored at −70° C.

Purification of PvMSP-1 p42 protein. All buffers used during purification were endotoxin free and kept chilled while the purification was carried out at room temperature. The *E. coli* cell paste was thawed (1:8 w/v) in chilled resuspension buffer (20 mM sodium phosphate (NaP), 500 mM NaCl, pH 7.4). Bacteria were lysed by microfluidization (Model 1109, Microfluidic Corp., Newton Mass.) and the soluble fraction was obtained after centrifugation at 15,000×g for 40 min at 4° C. The supernatant was further cleared by filtration through a 0.45μ filter and passed over a Ni-NTA Superflow column (Qiagen) (7 ml matrix per 40 gm paste) on a 600-E liquid chromatography system (Waters, Milford Mass.) at a flow rate of 2.5 ml min$^{-1}$. The column was washed with 40 mM imidazole contained in resuspension buffer until the $OD_{280}$ of the eluate stabilized. The column was equilibrated with 20 mM NaP buffer (pH 8.0) and PvMSP-1 p42 was eluted in the same buffer containing 500 mM imidazole (pH 8.0). Fractions containing the protein peak were pooled and diluted 5 fold in the elution buffer minus imidazole. This was loaded on a Q-Sepharose FAST-flow column (Amersham Pharmacia, Piscataway N.J.) (4 ml matrix per 40 gm paste) and the column was washed with 20 mM NaP buffer (pH 8.0), followed by the same containing 100 mM NaCl until the $OD_{280}$ stabilized. Pure PvMSP-1 p42 was eluted with 200 mM NaCl (pH 8.0) in 20 mM NaP buffer. Samples were dialyzed overnight against PBS at 4° C. and protein was estimated by Micro BCA protein assay reagent kit (Pierce, Rockford Ill.). Protein concentration was adjusted to 350 μg ml$^{-1}$ and stored in 150 μl aliquots (~50 μg per vial) at −70° C. Purified PvMSP-1 p42 was evaluated for homogeneity by densitometric analysis on reducing SDS-PAGE (4–12% NuPAGE; Invitrogen, Carlsbad, Calif.) with up to 20 μg protein loaded in a single well and stained with Coomassie blue. Absence of host *E. coli* specific proteins was further confirmed by western blotting with anti-*E. coli* polyclonal antibodies (Dako Corp. Carpinteria, Calif.).

Lyophilization and stability. Frozen aliquots of PvMSP-1 p42 protein were lyophilized for 24 h (Flex-Dry MP, FTS Systems, Stone Ridge N.Y.). Stability of the lyophilized material was checked by incubating freeze dried aliquots at −70° C., −30° C., 4° C., 25° C. and 37° C. respectively for up to 4 weeks. Samples at 24 hr, 48 hr, 72 hr, 1 wk and 4 wk were analyzed on non-reduced SDS-PAGE stained with Coomassie blue.

N-terminal sequencing, mass spectroscopy and disulphide analysis. Purified PvMSP-1 p42 protein was resolved on SDS-PAGE, transferred to a PVDF membrane and sequenced using Edman's degradation method. Protein samples were analyzed by Matrix Assisted Laser Desorption Ionization-Time of flight mass spectrometer (MALDI-TOF, Voyager Biospectrometery RP system, Applied Biosystems) using Sinapinic acid matrix. PvMSP-1 p42 protein was reduced in the presence of 10 mM DTT (BioRad, Richmond Calif.) and 6 M Guanidine HCl (Fisher Scientific, Fairlawn, N.J.) at 50° C. for 60 min. Alkylation was carried in the presence of 6M Guanidine HCl and 100 mM iodoacetamide (Sigma, St Louis Mo.) for 1 hr at 37° C. in the dark. Guanidine HCl was removed from samples by ethanol precipitation before analysis on Coomassie blue stained non-reduced SDS-PAGE for comparative mobility and on immunoblot for monoclonal antibody reactivity. Monoclonal antibodies raised against *P. vivax* MSP-1 p42 and p19 were kindly provided by Dr. Shirley Longacre (Pasteur Institute, Paris, France). Free sulfhydryl groups were estimated by Ellman's reagent (5,5'-Dithio-bis-(-3 Nitrobenzoic acid) (Lawrence etr al., 2000, Vaccine 18, 1925–1931). L-cysteine was used to plot the standard curve.

Immuoblotting and IFA. Immunoblotting was carried out using standard protocols and developed with a SuperSignal Chemiluminescent kit (Pierce, Rockford Ill.) or BM Blue POD substrate (Roche, Indianapolis Ind.). Rabbit anti-PvMSP-1 p42 antibodies were affinity purified using PvMSP-1 p42 coupled tosyl-activated magnetic beads (Dynal. Norway). IFA was done by standard protocols on methanol fixed blood smear of *P. vivax* Sal I strain infected Aotus monkey blood using fluorescein conjugated antibodies Endotoxin assay. Endotoxin levels were measured with the Limlus amebocyte lysate kit (Pyrochrome; Cape Cod Inc., Falmouth Mass.) using the end-point chromogenic method.

Mice immunization. Balb/c (H-$2^d$) and C57BL/6 (H-$2^b$) female mice, 6–8 wk old, were immunized with formulations containing PvMSP-1 p42 protein along with either Montanide ISA51 (M51) or Montanide ISA720 (M720) as adjuvant (Seppic Inc. Paris, France). Each formulation included 25 µg of protein with either 50% M51 or 70% by volume M720 adjuvant. Mice were immunized subcutaneously with 100 µl of the formulation, three times, with two-week interval between immunizations. Mice were euthanized 14 days after the last immunization; serum samples and spleens were collected. Control groups were immunized with the same amount of adjuvant in saline.

ELISA. Antibody responses against PvMSP-1 p42 protein were evaluated by an enzyme-linked immunosorbent assay (ELISA). Briefly, 96-well microplates (Dynax, Chantilly Va.) were coated with 100 ng per well of either reduced & alkylated or non-reduced PvMSP-1 p42 and kept overnight at 4° C., then blocked for 1 hr with PBS containing 0.05% Tween-20 (PBST) and 5% casein (Sigma, St. Louis, Mo.). Plates were washed three times and incubated for 2 hr at RT with individual and pooled mouse serum. Plates were washed again with PBST and 1:4000-diluted secondary anti-mouse IgG, IgG1, IgG2a, IgG2b or IgG3 horseradish peroxidase-labeled (HRP) antibodies (Southern Biotechnologies Associates, Birmingham, Ala.) were added for 1 hr. Plates were washed and developed with a 2,2'-azino-di (3-ethyl-benzthiazoline-6-sulfonate), ABTS-peroxidase substrate (Kirkegaard & Perry Laboratories, Gaithersburg Md.) and read at 405 nm. For determination of each IgG subclass, individual sera were tested in duplicate using 4-fold serial dilution, starting at 1:100.

Lymphoproliferative cellular responses. Spleens from mice were surgically removed from euthanized animals and a cell suspension was obtained by organ grinding in HBSS (Invitrogen). Leukocytes (pooled in each group) were resuspended, at $5 \times 10^6$ cells $ml^{-1}$, in Iscove's modified Dulbecco's medium (BioWhittaker, Walkersville Md.) supplemented with 0.5% normal mouse serum, 2 mM L-glutamine, 55 µM 2-mercaptoethanol, 1 mM sodium pyruvate, 0.1 mM non-essential amino acids and 100 units $ml^{-1}$ of penicillin-streptomycin (Invitrogen). One hundred (1 aliquots of the cell preparation were added to wells of a round-bottom 96-well plate. Cells were grown in the absence or presence of 0.1, 0.2, 0.5, 1.0 and 2.5 µM PvMSP-1 p42 or a control protein E. coli recombinant P. falciparum thrombospondin related adhesive protein (PfTRAP; manuscript in preparation) at 0.5 µM concentration. Positive control cultures were included on each plate and were stimulated with 2 µg $ml^{-1}$ of concanavalin A (Con A) after 48 hr. Cultures at final volume of 200 µl per well, were grown for 5 days at 37° C. under humidified atmosphere and 5% $CO_2$. Splenocytes were pulse-labeled during the final 16 hr with 1 µCi per well of tritiated thymidine (Amersham Pharmacia Biotech, Piscataway N.J.) and were harvested onto glass-fiber filters for liquid scintillation counting (cpm). Stimulation indexes were calculated as: Stimulation index (SI)=cpm test antigen (cpm control.

Cytokine production. Pooled cells were cultured at 37° C. under humidified atmosphere and 5% $CO_2$ in presence of 0.5 µM PvMSP-1 p42 or PfTRAP antigen in 24-well plates, at $2.5 \times 10^6$ cells per well, and supernatants collected after 48, 72, and 96 hr and screened for presence of IL-2, IL-4, IL-10, and IFN-γ using the respective Quantikine(M sandwich EIA kit (R&D systems Inc., Minneapolis Minn.). Control and sample values were read off the standard curve.

Statistical analysis: Data was processed using Microsoft Excel 2000® software. Linear regression analysis was used to calculate the serum dilution needed to give an OD equal to the mean plus 3 standard deviation (SD) of the negative controls. An analysis of variance test was used to determine the level of significance of the differences observed between groups.

EXAMPLE 1

Origami™(DE3) strain of E. coli enhances the expression of soluble PvMSP-1 p42. The PvMSP-1 p42 gene encoding 380 amino acids # 1350–1729 of the published sequence (Lilie et al., 1998, Curr. Opin. Biotechnol. 9, 497–67) was cloned in pETAT(NK2) vector. The insert was sequenced on both DNA strands and no amino acid differences were found when compared to the published sequence. Two E. coli host strains BL21(DE3) and Origami™(DE3) were tested for the production of soluble PvMSP-1 p42 protein. Both host strains were transformed with the same recombinant plasmid, grown, induced under identical fermentation conditions and PvMSP-1 p42 protein expressed in the soluble and insoluble fraction was partially purified under identical conditions (FIG. 1A). Recombinant PvMSP-1 p42 protein produced in E. coli had an apparent MW of ~50 kDa under reducing conditions. Densitometric analysis of the ~50 kDa band from both purifications showed that total PvMSP-1 p42 production was 15% better in Origami™(DE3) (compare lanes 1&2 with 3&4). In addition, origami™(DE3) cells contained 60% more protein in the soluble fraction compared to BL21(DE3) host cells (compare lanes 1 & 3). The soluble to insoluble PvMSP-1 p42 ratio for Origami™(DE3) was 8:1 whereas it was 0.4:1 for the BL21(DE3) strain. Therefore, the Origami™(DE3) strain was chosen for process development of PvMSP-1 p42 fermentation and purification.

EXAMPLE 2

The production and purification protocol is rapid and scalable. Fermentation conditions described earlier were found optimal for soluble protein production. On average 150 gm of wet cell mass was harvested from 10 L fermentation culture.

Figure 1B:
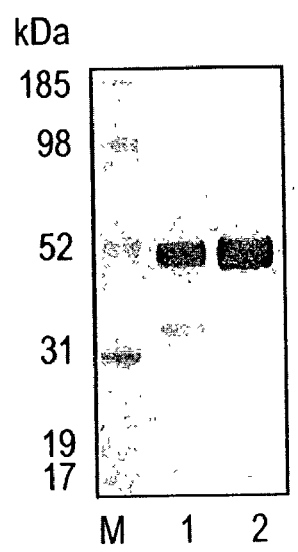
Figure 1C:
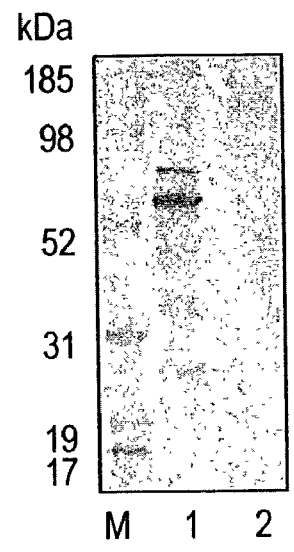

Purification was initiated by lysis and separation of the soluble fraction by centrifugation. The soluble fraction was loaded on a $Ni^{+2}$ column for initial purification. The column was washed with resuspension buffer containing 40 mM imidazole and PvMSP-1 p42 protein eluted off the $Ni^{+2}$ column was >80% pure (FIG. 1B, lane 1). Fractions containing the protein were pooled and diluted 5 fold to reduce the imidazole concentration before loading onto a Q-Sepharose anion-exchanger. Impurities either flowed through the Q-Sepharose column or were removed in the 100 mM NaCl wash. Purified PvMSP-1 p42 was eluted in 200 mM NaCl (pH 8.0) with final yield of 80–100 mg PvMSP-1 p42 per 10 L fermentation. Densitometeric analysis of the final products from independent purification experiments, showed >99% pure full-length product on reduced Coomassie blue stained SDS-PAGE (FIG. 1B, lane 2). Host E. coli protein content of 1000 µg $ml^{-1}$ pure PvMSP-1 p42 preparations was routinely below 1 µg $ml^{-1}$ (minimum detection limit) as measured by immunoblot (FIG. 1C, lane 2). Purity evaluation by HPLC gel-filtration and reversed-phase columns detected a single symmetrical peak in the final PvMSP-1 p42 preparations (data not shown).

EXAMPLE 3

Purified Recombinant PvMSP-1 p42 has a low endotoxin content. The final product was analyzed by the LAL assay for the presence of endotoxins. The final preparation of PvMSP-1 p42 protein contained between 30–50 EU's per 50 μg protein (estimated single human dose).

EXAMPLE 4

Purified Recombinant PvMSP-1 p42 is stable. Stability of PvMSP-1 p42 was estimated by incubating lyophilized protein at different temperature conditions and analyzing the protein by SDS-PAGE over a four wk period. PvMSP-1 p42 protein in its lyophilized form was found to be stable at −70° C., −30° C., 4° C., 25° C. and 37° C. with no signs of breakdown or aggregation (data not shown). Dimers and multimers were observed upon storage in PBS solutions at 4° C. for more than a wk.

EXAMPLE 5

Figure 2A:
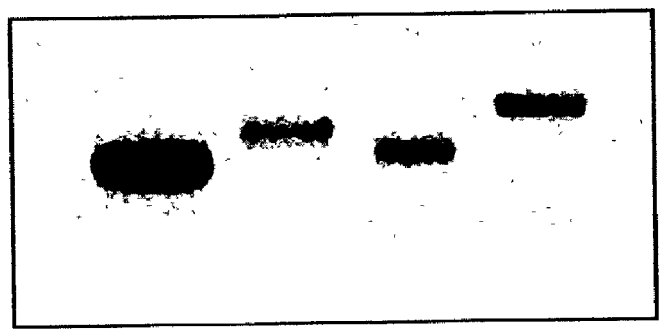
FIGS. 2A and 2B. (A) Coomassie blue stained non-reduced SDS-PAGE of purified PvMSP-1 p42 (~2 µg protein per well). Lanes: 1, non-reduced; 2, alkylated; 3, reduced; 4, reduced & alkylated. (B). Immunoblot with anti-PvMSP-1 monoclonal antibodies (shown above the lanes). Lanes: n, non-reduced protein; r, reduced & alkylated protein.

Recombinant PvMSP-1 p42 has the correct primary and tertiary structure. N-terminal sequencing of the final product using Edman degradation revealed the first 23 amino acids to be: Ala His His His His His His Pro Gly Gly Ser Gly Ser Gly Thr Met Ala Asp Gln Val Thr Thr Gly (17 amino acids encoded by the vector (SEQ ID NO:8); 6 PvMSP-1 p42 specific residues are shown in bold). MALDI-TOF MS showed a peak at 45,031 Da. Theoretical MW of the full length PvMSP-1 p42 is 45,035. Coomassie blue stained, non-reducing SDS-PAGE of freshly purified PvMSP-1p42, revealed a tight homogenous band (FIG. 2A, lane 1), indicating it is largely composed of a single conformer. Due to the presence of an odd number of 11 cysteines in PvMSP-1 p42 it is most likely that at least one cysteine was not involved in disulphide bond formation. This was further evidenced by a slight decrease in mobility of alkylated protein (FIG. 2A, lane 2). Alkylation of the native protein resulted in a mass increment of 58 amu's measured by MALDI-TOF MS which corresponds to the addition of a single alkyl-amide group to the protein. Reduction of PvMSP-1 p42 with DTT (FIG. 2A, lane 3) and its reductive-alkylation (FIG. 2A, lane 4) caused decreased mobility on SDS-PAGE indicating that other alkylation sites were accessible only upon breaking the disulphide bonds. Ellman's test for free sulfhydryls performed on pure PvMSP-1 p42 revealed 1.07 μmoles of free—SH per μmole of PvMSP-1 p42.

Figure 2B:
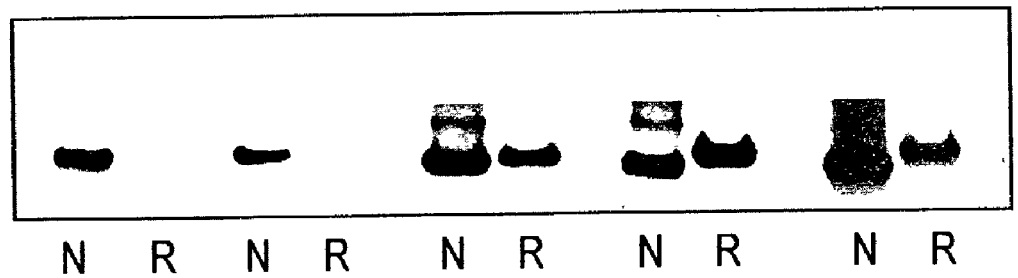

The presence of reduction sensitive epitopes was confirmed by reactivity to previously characterized monoclonal antibodies raised against PvMSP-1 p42 and p19 expressed by baculovirus. Monoclonals E9.14 and F10.3 recognize conformational disulphide bond dependent epitopes in the p19 region. Monoclonal 5.14 also recognizes a putatively conformational epitope on p42. The *E. coli* produced soluble PvMSP-1 p42 was recognized by all three of these monoclonals on non-reduced western blots (FIG. 2B). The reactivity to monoclonals 5.14 and E9.14 was reduced after reduction and alkylation (FIG. 2B; compare n and r). Monoclonal F10.3 showed decreased reactivity with reduced PvMSP-1 p42. A *P. falciparum* MSP-1 specific monoclonal was used as a negative control and showed no reactivity to PvMSP-1 p42 (data not shown). Reactivity was also seen with monoclonals F20.14 and D14, both of which recognize linear epitopes in the p42 and to a polyclonal sera from rabbit immunized with p19 (data not shown).

EXAMPLE 6

Figure 3:
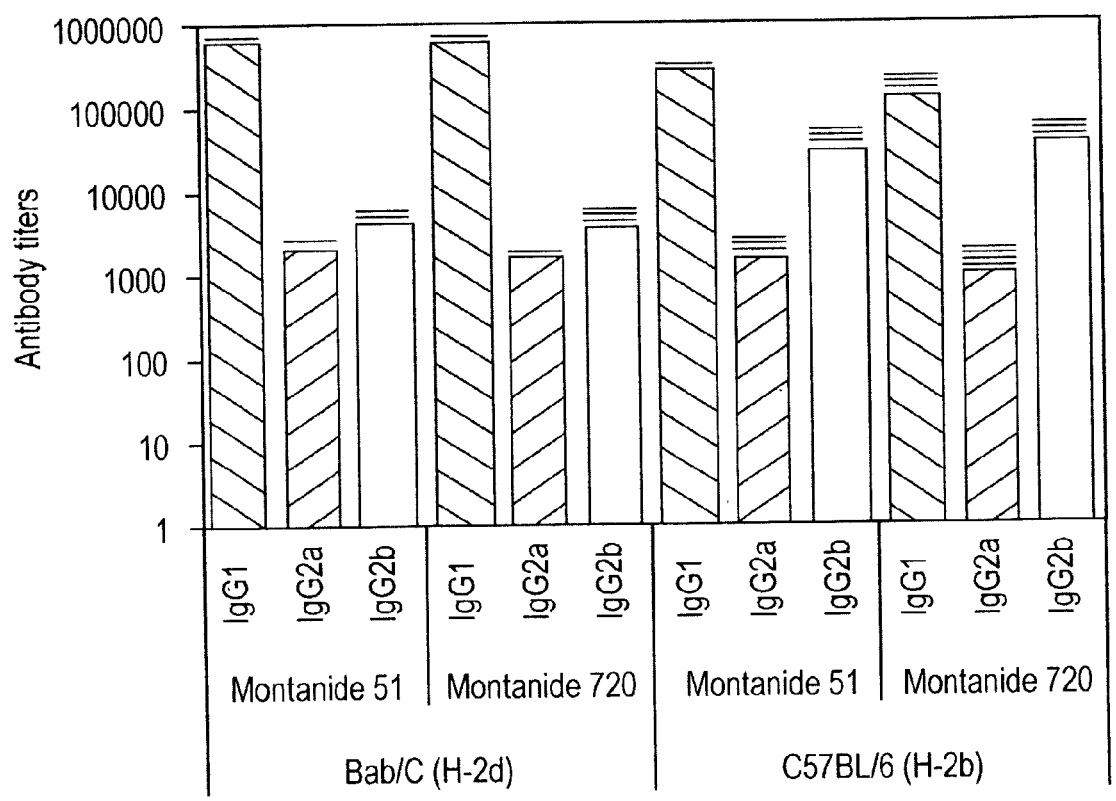
FIG. 3. IgG subclass antibody response in mice immunized with PvMSP-1 p42. Antibody titers are shown as the logarithmic values of the mean dilution plus standard deviation (boxes and lines) that have an OD of 0.1.

PvMSP-1 p42 induces specific antibody responses in immunized mice. Vaccination with PvMSP-1 p42 elicited a strong antibody and T cell response and was well tolerated in mice with no apparent signs of lesion formation. Individual sera from 4 animals in each group were tested for anti-PvMSP-1p42 IgG, IgG1, IgG2a, IgG2b and IgG3 by ELISA. The mean OD value plus 3 SD of the controls (using both strains and all anti-IgG subclasses at 1:100 dilution) was 0.080 (mean=0.030, SD=0.016). An OD cutoff value of 0.1 was selected for antibody titer determination. The dilution that gave an OD of 0.1 was determined using regression analysis on the linear portion of the curve for each serum. Mean end-point titers of each immunized group are shown on FIG. 3. All 4 PvMSP-1 p42 immunized groups showed high IgG titers with IgG1 being the highest (above $2 \times 10^5$), followed by IgG2b, IgG2a and IgG3 (data not shown) in that order. For each mouse strain, both adjuvants gave similar antibody response with some differences in the level of IgG1 and IgG2b between the two strains. Regardless of the adjuvant used, Balb/C mice produced about 3.5 times more IgG1 antibodies than the C57BL/6 group. Conversely, C57BL/6 mice produced about 6 times more IgG2b antibodies. These differences were statistically significant ($F>16.7$, $p<0.001$). Total IgG titers were also determined using reduced and alkylated PvMSP-1 p42 as coating antigen. OD values were 30–80% lower for all groups against reduced and alkylated protein.

EXAMPLE 7

PvMSP-1 p42 induces T cell responses in the immunized mice. TABLE 1, summarizes the cellular responses found in PvMSP-1 p42 immunized groups. As seen with the antibody response, the T cell stimulation indexes were similar in immunized groups of the same strain regardless the adjuvant used ($F<1.4$, $p>0.26$). The SI for the Balb/c group were however, higher than those for the C57BL/6 ($F=94.5$, $p<0.0001$) regardless the adjuvant used. Cytokine levels were measured in the culture supernatant from stimulated splenocytes after 48 and 72 hr of stimulation with PvMSP-1 p42. In general, Balb/c showed higher cytokine levels except for IFN-γ production in C57BL/6 mice. Nanogram levels of IFN-γ were observed in all groups with higher levels in the M720 immunized groups (see TABLE 1). Cells stimulated with the control protein (PfTRAP) showed undetectable levels of IL-2, IL-4, IFN-γ and 135 (31 pg ml$^{-1}$ of IL-10.

TABLE 1

Lymphoproliferative and cytokine responses in mice immunized with PvMSP-1 p42.

| Mice MHC | Adjuvant | Stimulation Index[1] | IL-2 | IL-4 | IL-10 | IFN-γ |
|---|---|---|---|---|---|---|
| | | | (pg/ml of supernatant)[2] | | | |
| H-2$^d$ | Montanide 51 | 5.9 ± 0.6 | 211 ± 11 | 59 ± 8 | 607 ± 51 | 2826 ± 1034 |
| H-2$^d$ | Montanide 720 | 6.2 ± 0.5 | 137 ± 22 | 46 ± 2 | 832 ± 31 | 3895 ± 914 |

TABLE 1-continued

Lymphoproliferative and cytokine responses
in mice immunized with PvMSP-1 p42.

| Mice | | Stimulation | IL-2 | IL-4 | IL-10 | IFN-γ |
|---|---|---|---|---|---|---|
| MHC | Adjuvant | Index[1] | (pg/ml of supernatant)[2] | | | |
| H-2[b] | Montanide 51 | 3.3 ± 0.2 | 37 ± 4 | 29 ± 0 | 658 ± 10 | 1104 ± 180 |
| H-2[b] | Montanide 720 | 3.8 ± 0.4 | 43 ± 8 | 17 ± 8 | 761 ± 44 | 5135 ± 1016 |

[1]Data shows the SI (mean value and the standard deviation) of cells stimulated with 0.2, 0.5, 1.0 and 2.5 μM PvMSP-1 p42. Background average count for cells stimulated with the control *P. falciparum* PfTRAP antigen was 4365 (1504 cpm for Balb/c (H-2[d]) and 4903 (1875 for C57BL/6 (H-2[b]). Similar scintillation counts were observed in cells from adjuvant control groups stimulated with PvMSP-1 p42 protein (data not shown). Stimulation with Con A gave count above 60,000 cpm.
[2]Peaks of cytokine production detected in cell culture supernatant after 48 and 72 h of in vitro stimulation with 0.5 μM PvMSP-1 p42.

EXAMPLE 8

Figure 4A:
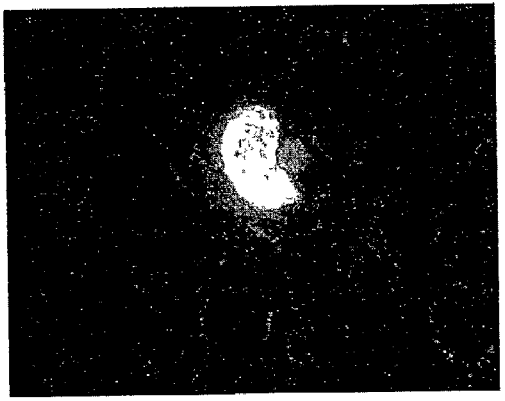
FIGS. 4A and 4B. (A) Fluorescence and phase images of a methanol fixed *P. vivax* Sal I strain parasite (early schizont) on a Aotus monkey blood smear, immuno-stained with affinity purified anti-PvMSP-1 p42 antibody raised in rabbit. (B) Fluorescence and phase image of a late trophozoite stage of *P. vivax* Sal I parasite, immuno-stained with pooled anti-PvMSP-1 p42 sera from the Balb/C mice in M51 group.
Figure 4A:
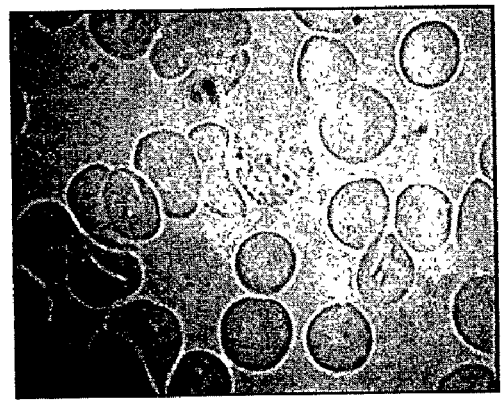
Figure 4B:
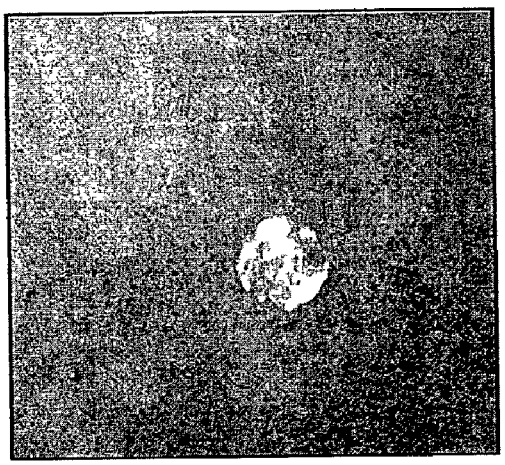
Figure 4B:
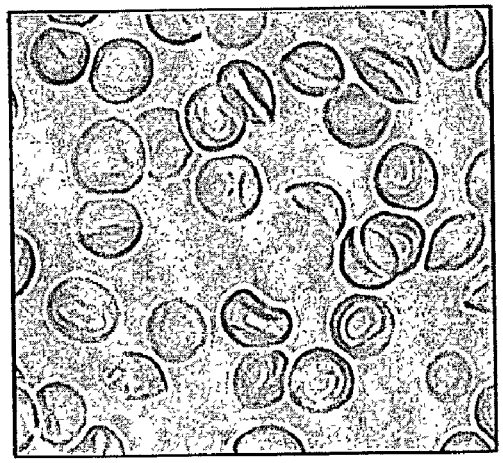

Recombinant PvMSP-1 p42 resembles the native parasite protein. Affinity purified rabbit anti-PvMSP-1 p42 antibodies tested positive by IFA against blood stages of *P. vivax* Sal I strain. FIG. 4A shows an early schizont with bright fluorescence. Polyclonal antibodies in all PvMSP-1 p42 immunized mice groups also tested positive on IFA. FIG. 4B shows a late trophozoite stage stained by pooled serum from Balb/C immunized PvMSP42-1 p42 and M51. No recognition was found using control sera.

DISCUSSION

Merozoite surface protein-1 is one of the most important vaccine candidates from the blood stage of malarial parasite. There is evidence of the protective role of MSP-1 in rodent and simian models of malaria. Advanced evaluation of such a promising antigen in human volunteers requires process development for the production of pharmaceutical grade recombinant MSP-1. Here we present a process that can be used for large-scale production of recombinant *P. vivax* MSP-1 p42 protein in *E. coli*. Although vaccination with the p19 region of MSP-1 has been shown to protect animals we have chosen to express the entire p42 domain, as the p33 portion contains some important B and T cell determinants (Kaslow and Kumar, 1996, supra). Moreover, we believe that the p33 region provides a hydrophilic scaffolding for the correct folding of the p19, just as GST fusion p19 constructs have been previously shown to fold correctly in *E. coli* (Ling et al., 1994, Parasite Immunol. 16, 63–67).

Prokaryotic expression systems like *E. coli* produce large quantities of protein with a relatively simple fermentation protocol. This system shares an important feature with *Plasmodium* in that it lacks N-glycosylation (Ling et al., 1995, Parasite Immunol. 17, 425–433). However, one of the major drawbacks of *E. coli* is the reducing nature of its cytoplasm, which inhibits the formation of disulfide bridges, and may result in incorrect folding of complex proteins or formation of protein aggregates. MSP-1 contains a cysteine rich (p19) domain with 5 to 6 disulphide bonds (depending on the species). The presence of correctly formed disulphide bonds in the p19 region has been shown to be critical for the induction of protective immune response against the parasite in animal models (Ellman, G. L., 1959, supra; Gibson et al., 1992, supra). Although PvMSP-1 p42 can be expressed in a conventional *E. coli* host BL21(DE3), a large portion of the product was insoluble. Attempts to improve solubility by varying fermentation conditions were unsuccessful. We then focused on expressing this gene in 'redox modified' hosts such as AD494 (Novagen), a thioredoxin reductase (trxB) mutant host. The protein solubility however, showed no substantial improvement. Recently an *E. coli* host strain, Origami™: a thioredoxin and glutathione reductase (gor) gene mutant (Dieckmann-Schuppert et al., 1992, supra), was shown to promote disulphide bond formation within the cell cytoplasm. Using this host strain we achieved significant enhancement in the yield of soluble PvMSP-1 p42. Furthermore, a combination of low IPTG concentration and low temperature induction was found to favor expression of soluble PvMSP-1 p42, probably caused by reduction in the rate of protein synthesis (Besette et al., 1999, supra). The above strategy might be useful in improving the yield of other vaccine antigens expressed in *E. coli*.

The *E. coli* expression vector pETAT(NK2) used here is a derivative of vector pET32 and has been specially engineered for the production of vaccine candidate antigens in *E. coli*. The plasmid was constructed to have a tet$^r$ gene for selection during fermentation, because ampicillin is not a preferred antibiotic for use in the manufacture of human use products. This raised an important issue when a switch to Origami™ cells was made, as this strain is tetracycline resistant. Using a series of fermentation experiments and colony counts we confirmed that there was no significant plasmid loss and decline in protein yield when tetracycline was used during fermentation, in comparison to ampicillin.

The purification scheme described here is rapid and the whole process from cell lysis to elution of the final product can be carried within two days. Purification can be carried out at room temperature and is designed for easy scale-up. The two-step purification comprises step-wise increments in eluent concentrations during wash and elution instead of continuous gradients; this was done to make the process robust and facilitate reproducibility. The process gives greater than 99% pure PvMSP-1 p42 protein with an endotoxin content within permissible levels for an injectable pharmaceutical.

We have used multiple techniques to determine the purity of the product. Reduced SDS-PAGE analysis with over-loaded (up to 20 μg per well) protein and immuno-blotting with an anti-*E. coli* antibody confirmed high level of purity of the product. In addition the protein was also found to be homogenous by HPLC analysis on reversed-phase and gel filtration columns with no signs of aggregation (data not shown). PvMSP-1 p42 was found to be stable at room temperature in its lyophilized form. Primary structure was confirmed by N-terminal sequencing and mass-spectrometer analysis. The N-terminal methionine could not be identified during sequencing, however the 23 subsequent amino-acids including six PvMSP-1 specific residues were confirmed by N-terminal sequencing. The molecular weight of PvMSP-1 p42 was found to be within 4 amu's of the predicted mass. We have confirmed the presence of a predicted free cysteine in the final product. The protein was also recognized by monoclonal antibodies against conformational and linear epitopes on a baculovirus expressed PvMSP-1 (Collins et al., 1999, supra).

Immunogenicity of PvMSP-1 p42 was carried out in mice using two metabolizable oil based adjuvants: Montanide ISA51 and ISA720. The two adjuvants differ in the surfactant content with M720 forming thinner emulsions. Both adjuvants are generally considered safe for human use and have been applied to malaria vaccine trials in monkeys and humans (Long et al., 1994, Am. J. Trop. Med. Hyg. 50(Suppl), 27–32; Longacre et al., 1994, Mol. Biochem. Parasitol. 64, 191–205; Patterson et al., 1999, Vaccine 18, 173–180). Vaccination with both adjuvants induced IgG1, IgG2a and IgG2b antibodies along with the production of cytokines IL-4, IL-10 and IL-2, IFN-γ. Cytokines IL-2 and IFN-γ are associated with the production of IgG2a and are indicators of T helper-1 cell (Th1) activation and of predominately cell-mediated response; in contrast IL-4 and IL-10 cytokines secreted by T helper-2 cells (Th2) are associated with the production of IgG1 and indicate an antibody mediated response (Perera et al., 1998, Infect. Immun. 66, 1500–1506). Results indicate that both Th1 and Th2 subsets of T helper cells are being elicited by PvMSP-1 vaccination. The activation of both subsets of Th cells, sometimes with one response dominating the other, has been shown to correlate with protection against blood stage challenge in murine models (Perlaza et al., 1998, Infect. Immun. 66, 3423–3428; Saul et al., 1999, Vaccine 17, 3145–3159). An ideal blood stage vaccine candidate would be one that can activate both Th1 and Th2 responses (Sjolander et al., 1995, Immunology 84, 360–366; Soares et al., 1997, Infect. Immun. 65, 1606–1614).

Immunization in two strains of mice with the two adjuvants showed comparable B and T responses with M720 showing higher levels of IFN-γ in both strains of mice. We plan to go forward with M720 in a future study of immune response in rhesus monkeys. The difference in cytokine response and IgG profile observed between the two strains indicates some genetic restriction of immune response against PvMSP-1 p42 as seen for several other *Plasmodium* antigens (Taylor-Robinson et al., 1993, Science 260, 1931–1934).

Reactivity of sera from all the groups was 30–80% lower with reduced PvMSP-1 p42 compared to the native protein. A similar observation was made with human immune sera against *P. vivax*, where titers were on average 50% less against reduced p19 (Yang et al., 1999, Infect. Immun. 67, 342–349). This indicates a large contribution of conformational epitopes in the overall antibody response against PvMSP1 p42. The generation of such conformational anti-MSP-1 antibodies is critical to raise a protective response against the parasite (Ellman, G. L., 1959, supra; Gibson et al., 1992, supra). Rabbit and mouse antibodies raised against PvMSP-1 p42 protein reacted with native MSP-1 on the parasite by IFA, further establishing the near native structure of PvMSP-1 p42. Recombinant PvMSP-1 p42 protein also reacted positively with sera collected from a *P. vivax* endemic area on Western blot and ELISA (data not shown).

The process development efforts described here are a critical part of the development of a subunit vaccine and address some of the issues facing protein chemists involved in production of protein based pharmaceuticals. The availability of clinical grade antigens will help in establishing the efficacy of promising antigens like PvMSP-1 p42 as a part of a human malaria vaccine, and serve as a reagent for immunological and functional studies.

What is claimed is:

1. A recombinant non-glycosylated *Plasmodium vivax* Sal I merozoite surface protein-1 (PvMSP-1) p42 [which retains its native conformational epitopes] identified in SEQ ID NO:2.

2. A composition comprising the recombinant PvMSP-1 p42 of claim 1.

3. A recombinant protein according to claim 1, wherein said protein is at least 95% pure.

4. A recombinant protein according to claim 1, wherein said protein is at least 96% pure.

5. A recombinant protein according to claim 1 wherein said protein is at least 97% pure.

6. A recombinant protein according to claim 1 wherein said protein is at least 98% pure.

7. A recombinant protein according to claim 1 wherein said protein is at least 99% pure.

8. A kit for determining the presence of malaria antibodies in a biological sample comprising:
   the protein according to claim 1,
   a buffer or components necessary for producing a buffer; and
   reagents for detecting immune complexes formed between the protein and antibodies present in the sample.

9. A kit for monitoring malaria infection or prognosing the response to treatment of patients suffering from malaria infection comprising: the PvMSP-1 p42 protein according to claim 1, a buffer reagents for detecting the immune complexes formed between the protein and antibodies present in the sample, and optionally, additional reagents for determining the amount of immune complex formed.

10. A vaccine against malaria comprising *P. vivax* MSP-1 p42 according to claim 1.

11. The vaccine of claim 10 wherein said *P. vivax* is chosen from the group consisting of Belem, Chesson, Vietnam, and North Korean.

12. The vaccine of claim 11 further comprising an adjuvant.

13. The vaccine of claim 12 wherein said adjuvant is chosen from the group consisting of: montanide and alum.

14. The vaccine of claim 11 further comprising another antigen selected from the group PvCSP Type 210, PvCSP Type 247, PvTRAP, PvMSP2, PvMSP4, PvMSP5, PvMSP6, PvMSP7, PvMSP8, PvMSP9, and PvAMA1.

\* \* \* \* \*